US011003883B2

(12) United States Patent
Aronoff-Spencer et al.

(10) Patent No.: US 11,003,883 B2
(45) Date of Patent: May 11, 2021

(54) ADJUSTABLE FINGERPRINT CAPTURING DEVICE

(71) Applicant: THE REGENTS OF THE UNIVERSITY OF CALIFORNIA, Oakland, CA (US)

(72) Inventors: Eliah Aronoff-Spencer, La Jolla, CA (US); Tom Kalisky, La Jolla, CA (US); Isaiah Freerksen, La Jolla, CA (US); Deborah Forster, La Jolla, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 200 days.

(21) Appl. No.: 15/914,948

(22) Filed: Mar. 7, 2018

(65) Prior Publication Data
US 2018/0260603 A1    Sep. 13, 2018

Related U.S. Application Data

(60) Provisional application No. 62/467,971, filed on Mar. 7, 2017.

(51) Int. Cl.
*G06K 9/00* (2006.01)
*G16H 10/60* (2018.01)
(Continued)

(52) U.S. Cl.
CPC ....... *G06K 9/00013* (2013.01); *G06K 9/0002* (2013.01); *G06K 9/0004* (2013.01);
(Continued)

(58) Field of Classification Search
CPC ............. G06K 9/0002; G06K 9/00013; G06K 9/00006; G06K 9/228; G06F 21/32; G06F 3/0414; G06Q 20/40145
See application file for complete search history.

(56) References Cited

U.S. PATENT DOCUMENTS 3,804,524 A * 4/1974 Jocoy .................. A61B 5/1172
356/138
6,162,486 A * 12/2000 Samouilhan ......... A61B 5/1172
118/31.5
(Continued)

OTHER PUBLICATIONS

Jain et al., Biometrics for Child Vaccination and Welfare: Persistence of Fingerprint Recognition for Infants and Toddlers, MSU Technical Report MSU-CSE-15-7, Apr. 15, 2015, pp. 1-17.*
(Continued)

*Primary Examiner* — Guillermo M Rivera-Martinez
(74) *Attorney, Agent, or Firm* — Sheppard, Mullin, Richter & Hampton LLP

(57) ABSTRACT

An adjustable fingerprint capturing device is configured to stabilize a finger of a subject. The adjustable fingerprint capturing device comprises an imaging device(s) configured to capture an image(s) of the finger. The adjustable fingerprint capturing device comprises an image actuator. The adjustable fingerprint capturing device comprises a controller configured to activate the imaging device(s) based on input from the image actuator. The adjustable fingerprint capturing device comprises a housing disposed to: the imaging device(s), the image actuator, and the controller. The adjustable fingerprint capturing device comprises a plurality of moveable finger stabilizers configured to move about a portion of the housing. The plurality of moveable finger stabilizers are configured to apply pressure to the finger. The adjustable fingerprint capturing device comprises a stabilizer actuator connected to: the housing and the plurality of moveable finger stabilizers. The stabilizer actuator is configured to cause the plurality of moveable finger stabilizers to move.

21 Claims, 12 Drawing Sheets

(51) Int. Cl.
*G06K 9/03* (2006.01)
*G16H 40/20* (2018.01)

(52) U.S. Cl.
CPC ........... *G06K 9/00926* (2013.01); *G06K 9/03* (2013.01); *G16H 10/60* (2018.01); *G16H 40/20* (2018.01)

(56) References Cited

U.S. PATENT DOCUMENTS

| | | | | |
|---|---|---|---|---|
| 2002/0031245 | A1* | 3/2002 | Rozenberg | G06F 3/03543 |
| | | | | 382/125 |
| 2004/0101171 | A1* | 5/2004 | Lane | G06K 9/00013 |
| | | | | 382/124 |
| 2004/0208349 | A1* | 10/2004 | Ide | A61B 5/1172 |
| | | | | 382/124 |
| 2006/0110015 | A1* | 5/2006 | Rowe | G06K 9/00013 |
| | | | | 382/124 |
| 2007/0279187 | A1* | 12/2007 | Hekmatpour | G06Q 50/24 |
| | | | | 340/5.83 |
| 2010/0182126 | A1* | 7/2010 | Martis | A61B 5/1172 |
| | | | | 340/5.83 |
| 2011/0288874 | A1* | 11/2011 | Hinkamp | G06F 21/6245 |
| | | | | 705/1.1 |
| 2012/0177257 | A1* | 7/2012 | Maev | A61B 5/1172 |
| | | | | 382/124 |
| 2014/0103943 | A1* | 4/2014 | Dunlap | H01L 21/4857 |
| | | | | 324/663 |
| 2015/0070037 | A1* | 3/2015 | Pragada | G01R 1/06705 |
| | | | | 324/754.03 |
| 2015/0205992 | A1* | 7/2015 | Rowe | G06K 9/2018 |
| | | | | 382/124 |
| 2018/0068100 | A1* | 3/2018 | Seo | G06F 21/32 |
| 2018/0082024 | A1* | 3/2018 | Curbera | H04L 9/3236 |

OTHER PUBLICATIONS

Koda et al., Advances in Capturing Child Fingerprints: A High Resolution CMOS Image Srensor with SLDR Method, 2016 Gesellschaft für Informatik e.V., Bonn, Germany, pp. 1-4.*

* cited by examiner

ADJUSTABLE FINGERPRINT CAPTURING DEVICE

CROSS-REFERENCE TO RELATED APPLICATIONS

This application claims priority to U.S. Provisional Patent Application No. 62/467,971 filed on Mar. 7, 2017 and titled "Adjustable Fingerprint Capturing Device," which is incorporated herein by reference in its entirety.

BACKGROUND

Many existing fingerprint capturing devices may not be configured to consistently capture fingerprints on some subjects, especially infants and toddlers. Inconsistent fingerprint captures may lead to false identification of a subject. Employment of many existing fingerprint capturing devices may cause excessive torque (i.e. a rotational force) on the finger of the subject. Excessive torque on the finger during fingerprint capture may cause movement during fingerprint capture. Movement during fingerprint capture may reduce the ability to identify fingerprint features.

Many existing non-contact fingerprint capturing devices may not be configured to effectively keep the finger of a subject in a location necessary for an effective fingerprint capture.

What is needed is an improved fingerprint capturing device.

DETAILED DESCRIPTION OF EMBODIMENTS

Figure 1:
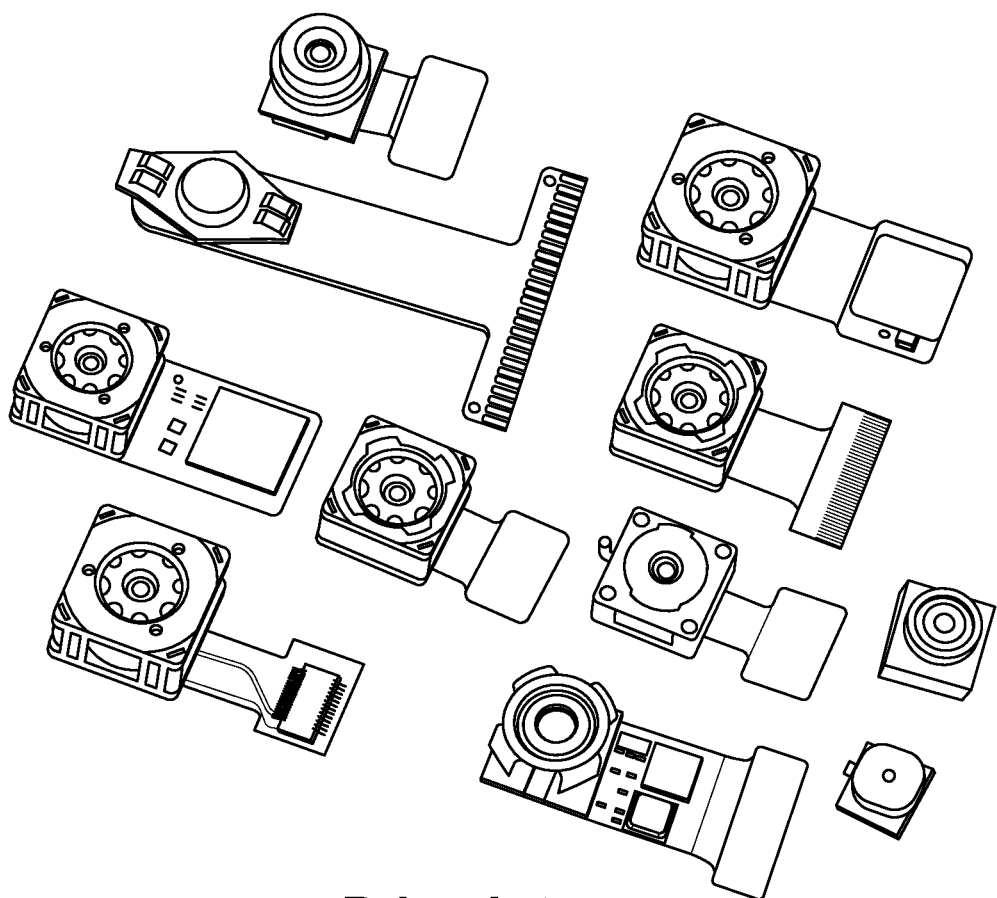
FIG. 1 illustrates example imaging devices according to various aspects of various embodiments.

Embodiments are employed to capture fingerprint images.

According to some of the various embodiments, an adjustable fingerprint capturing device may be configured to stabilize a finger of a subject. The subject may comprise an infant or a toddler. The adjustable fingerprint capturing device may comprise at least one imaging device. The at least one imaging device may be configured to capture at least one image of the finger of the subject. The adjustable fingerprint capturing device may comprise at least one image actuator. The adjustable fingerprint capturing device may comprise a controller. The controller may be configured to activate the at least one imaging device. The controller may be configured to activate the at least one imaging device based on input from the image actuator. The adjustable fingerprint capturing device may comprise a housing. The housing may be disposed to the at least one imaging device, the image actuator, the controller, combinations thereof, and/or the like. The adjustable fingerprint capturing device may comprise a plurality of moveable finger stabilizers. The plurality of moveable finger stabilizers may be configured to move about a portion of the housing. At least some of the plurality of moveable finger stabilizers may be configured to accept the finger of the subject between at least two of the plurality of movable finger stabilizers. The plurality of moveable finger stabilizers may be configured to apply pressure to the finger of the subject. The adjustable fingerprint capturing device may comprise a stabilizer actuator. The stabilizer actuator may be connected to the housing and the plurality of moveable finger stabilizers. The stabilizer actuator may be configured to cause the plurality of moveable finger stabilizers to move.

According to some of the various embodiments, at least one imaging device may be configured for contactless imaging. For the purposes of this disclosure, contactless imaging refers to no contact with the portion of a fingertip targeted in a fingerprint capture during capture of a fingerprint. The at least one imaging device may comprise a camera, an ultrasound device, combinations thereof, and/or the like. At least one of the at least one imaging device may comprise an optical scanner. At least one of the at least one imaging device may be configured to capture images with a resolution in the range of 3,000 to 10,000 PPI. At least one of the at least one imaging device may be configured to capture multiple 2D images. The 2D images may be employed for rendering at least one 3D image. The at least one imaging device may be configured to communicate image data to a controller and/or remote device via a wired and/or wireless connection. At least one of the at least one imaging device may comprise at least one liquid lens.

According to some of the various embodiments, at least one image actuator may comprise a button, a switch, at least one detection sensor, combinations thereof, and/or the like. The at least one detection sensor may be configured to detect presence of a finger of a subject. The at least one detection sensor may be configured to detect a pressure of a finger and/or a proximity of a finger.

According to some of the various embodiments, a housing may comprise at least one finger guide. The at least one finger guide may comprise at least one concaved surface configured to at least partially conform to the shape of a finger of a subject. The at least one finger guide may be configured to relax a finger of a subject. The at least one finger guide may be configured to keep a required orientation of a finger of a subject during image capture of at least one image.

According to some of the various embodiments, an adjustable fingerprint capturing device may comprise a plurality of moveable finger stabilizers. At least two of the plurality of moveable finger stabilizers may be configured to move along a portion of a housing. At least two of the plurality of moveable finger stabilizers may be configured to rotate around an axis connected to the housing. At least two of the plurality of moveable finger stabilizers may be configured to apply pressure to the sides of a finger of a subject. At least two of the plurality of moveable finger stabilizers may be configured to stabilize the sides of the finger and/or the first joint of the finger of the subject. At least two of the plurality of moveable finger stabilizers may be configured to relax the finger of the subject. At least two of the plurality of moveable finger stabilizers may be configured to equalize pressure across at least a portion of the finger of the subject. At least two of the plurality of moveable finger stabilizers may be configured to keep a required orientation of the finger of the subject during image capture of at least one image.

According to some of the various embodiments, a plurality of moveable finger stabilizers may be configured to keep a finger of a subject in place for at least one fingerprint capture. The plurality of moveable finger stabilizers may be configured to position the fingertip of the finger of the subject for a successful fingerprint capture. A successful fingerprint capture may comprise determination of at least one identifiable fingerprint feature. The moveable finger stabilizers may be configured to stabilize a fingertip in a non-deforming manner.

According to some of the various embodiments, a stabilizer actuator may be configured to cause activation of an image actuator. The stabilizer actuator may comprise a lever, a pin, a gear, an electromechanical device, a trigger, combinations thereof, and/or the like. The stabilizer actuator may be configured to cause a plurality of moveable finger stabilizers to move towards a finger of a subject. The lever and/or the pin may be configured to cause a plurality of moveable finger stabilizers to move upon receiving pressure on the lever and/or the pin from an operator of the adjustable fingerprint capturing device. The stabilizer actuator may be configured to cause the plurality of moveable finger stabilizers to move away from the finger of the subject. The lever and/or the pin may be configured to cause the plurality of moveable finger stabilizers to move away from the finger of the subject upon a reduction of pressure on the lever and/or the pin from an operator of the adjustable fingerprint capturing device.

According to some of the various embodiments, an adjustable fingerprint capturing device may comprise at least one moveable finger support plate. The at least one moveable finger support plate may be configured to support at least a portion of a palmar surface of a fingertip of a finger of a subject. The at least a portion of a palmar surface of a fingertip of a finger of a subject may be supported by the at least one moveable finger support plate prior to a fingerprint capture. The at least one moveable finger support plate may be employed to stabilize a finger position. For example, the at least one moveable finger support plate may be employed to prevent a subject from curling the finger prior to stabilization from a plurality of moveable finger stabilizers. According to some of the various embodiments, a stabilizer actuator may be connected to the at least one moveable finger support plate. The stabilizer actuator may be configured to cause the at least one moveable support plate to move. The stabilizer actuator may be configured to cause the at least one moveable finger support plate to move after a first pressure has been reached by the moveable finger stabilizers connected to the stabilizer actuator. For example, the stabilizer actuator may comprise a plurality of stabilizer springs and at least one support plate spring. The plurality of stabilizer springs may be connected to the plurality of moveable finger stabilizers. A first spring set may comprise at least some of the plurality of stabilizer springs. Springs in the first spring set may comprise a first spring rate and/or spring length. The at least one support plate spring may be connected to the at least one moveable support plate. A second spring set may comprise at least one of the at least one support plate spring. Springs in the second spring set may comprise a second spring rate and/or spring length. The stabilizer actuator may cause a first force to be applied to the first spring set. The first spring set may cause a first return force to be applied to at least a portion of the stabilizer actuator. The stabilizer actuator may be configured to cause a second force to be applied to the second spring set. The stabilizer actuator may be configured to cause the second force after the first return force exceeds a force threshold. The force threshold may be adjustable. The force threshold may be adjusted based on the size of the finger of the subject, the size of the moveable finger stabilizers, the size of the stabilizer actuator, combinations thereof, and/or the like. Movement of the at least one moveable support plate may cause the fingertip of the finger of the subject to be exposed to at least one image device. The movable finger support plate may be at least partially concave in relation to the finger of the subject. The at least one moveable support plate may be opaque.

According to some of the various embodiments, an adjustable fingerprint capturing device may comprise at least one fixed finger stabilizer. The at least one fixed finger stabilizer may be configured to apply pressure to the tip of a finger of a subject.

FIG. 1 illustrates example imaging devices 100 according to various aspects of various embodiments. An imaging device may comprise a camera. Imaging devices 100 may be configured to communicate with a controller via wired and/or wireless connections. A wired connection may comprise a circuit board, a circuit board slot, a bus, combinations thereof, and/or the like.

Figure 2:
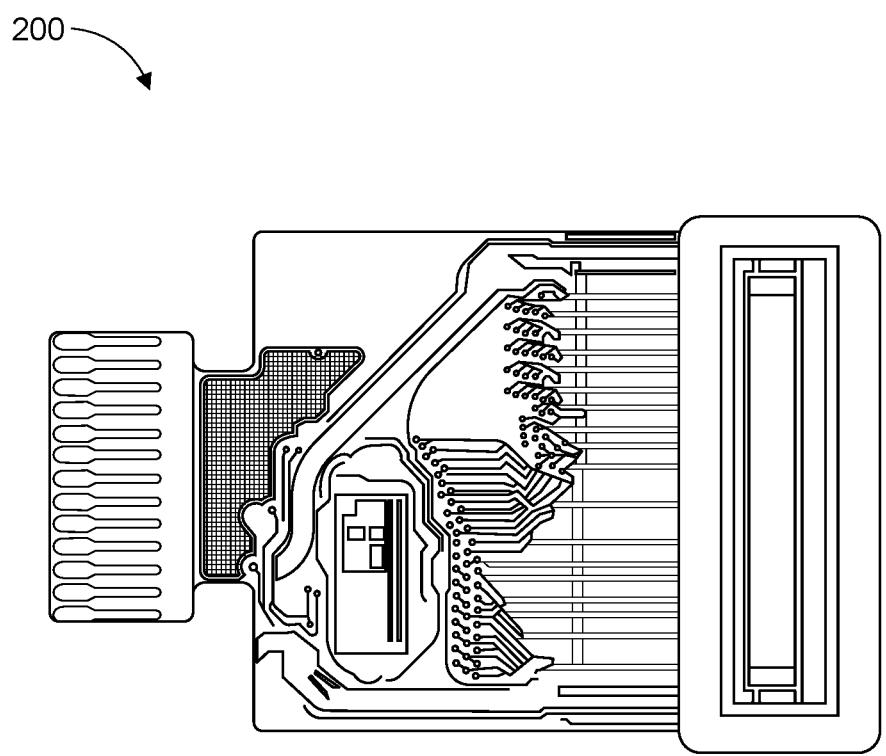
FIG. 2 illustrates an example imaging device as per an aspect of various embodiments.

FIG. 2 illustrates an example imaging device 200 as per an aspect of various embodiments. The imaging device 200 may comprise an ultrasound device.

Figure 3:
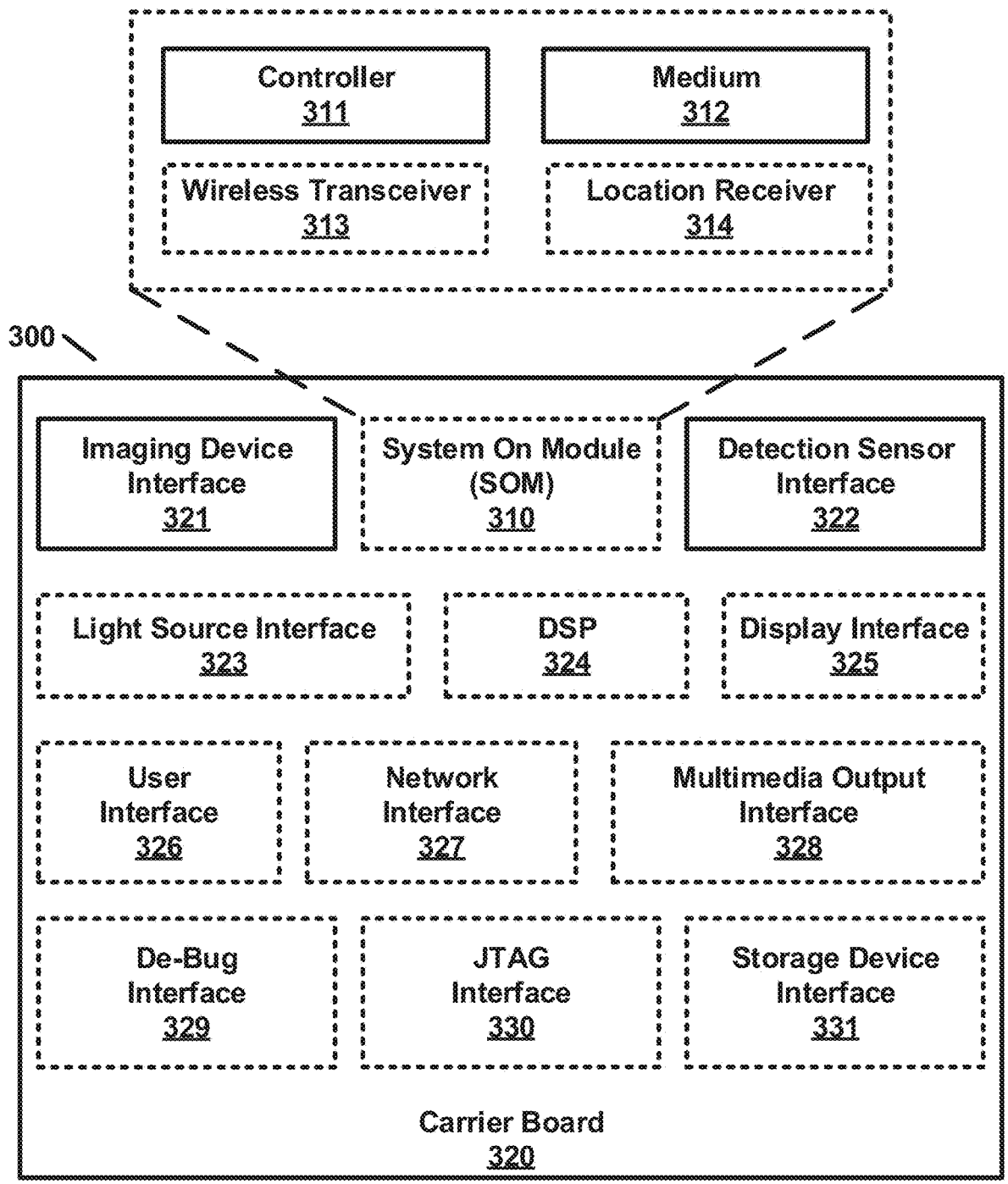
FIG. 3 is an example block diagram of a microprocessing environment in which aspects of embodiments of the present invention may be practiced.

FIG. 3 is an example block diagram of a microprocessing environment 300 in which aspects of embodiments of the present invention may be practiced. The microprocessing environment 300 may comprise a carrier board 320. The carrier board 320 may comprise a controller 311 and a computer readable medium 312. The controller 311 may comprise at least one processor. The controller 311 may comprise at least one power manager. Examples of computer readable medium 312 include Double Data Rate Synchronous Dynamic Random-Access Memory (DDR SDRAM), flash memory, at least one Solid State Drive (SSD), combinations thereof, and/or the like. An example of flash memory includes an embedded Multi-Media Controller (eMMC).

Microprocessing environment 300 may comprise a wireless transceiver 313. The wireless transceiver 313 may be configured to communicate with other components of the microprocessing environment 300 and/or at least one remote device. For example, the wireless transceiver 313 may be configured to communicate with at least one imaging device, at least one detection sensor, at least one light source, at least one display device, at least one storage device, combinations thereof, and or the like. Examples of remote devices include computers, laptops, tablets, smartphones, combinations thereof, and/or the like. The wireless transceiver 313 may be configured to communicate through employment of a Wireless Local Area Network (WLAN), a Bluetooth connection, a 4th Generation Long Term Evolution (4G LTE) network, a Wi-Fi network, Frequency Modulation (FM) signals, combinations thereof, and/or the like. The microprocessing environment 300 may comprise a location receiver 314. An example of the location receiver 314 includes a Global Navigation Satellite System (GNSS) receiver. The microprocessing environment 300 may comprise a System On Module (SOM) 310. The SOM 310 may comprise the controller 311 and the medium 312. The SOM 310 may comprise the wireless transceiver 313. The SOM 310 may comprise the location receiver 314.

Carrier board 320 may comprise an imaging device interface 321. The imaging device interface 321 may be configured to communicate and/or interpret communication with at least one imaging device. The carrier board 320 may comprise a detection sensor interface 322. The detection sensor interface 322 may be configured to communicate and/or interpret communication with at least one detection sensor. The carrier board 320 may comprise a light source interface 323. The light source interface 323 may be configured to communicate and/or interpret communication with at least one light source. The carrier board 320 may comprise a Digital Signal Processor (DSP) 324. An example of the DSP 324 includes a Qualcomm Hexagon QDSP6. The carrier board 320 may comprise a display interface 325. The display interface 325 may be configured to communicate and/or interpret communication with at least one display device. One of the at least one display device may be disposed to a housing disposed to the carrier board 320. The display interface 325 may comprise a Graphics Processing Unit (GPU).

Carrier board 320 may comprise a user interface 326. The user interface 326 may be configured to communicate with external devices. The user interface 326 may be configured to communicate through employment of a Universal Serial Bus (USB) connection, a FireWire connection, a Thunderbolt connection, combinations thereof, and/or the like. The carrier board 320 may comprise a network interface 327. The network interface 327 may be configured to communicate with external networks. The network interface 327 may be configured to communicate through employment of a Ethernet or Gigabit Ethernet connection. The carrier board 320 may comprise a multimedia output interface 328. The multimedia output interface 328 may be configured to communicate image information, video information, audio information, combinations thereof, and/or the like to external devices such as display devices, speakers, headphones, combinations thereof, and/or the like. The multimedia output interface may comprise an HDMI port, a Thunderbolt port, a DisplayPort, speaker ports, a headset port, combinations thereof, and/or the like.

Carrier board 320 may comprise a de-bug interface 329. The de-bug interface 329 may be employed to de-bug components of the microprocessing environment 300. The carrier board 320 may comprise a Joint Test Action Group (JTAG) interface 330. The JTAG interface 330 may be employed to de-bug components of the microprocessing environment 300. The carrier board 320 may comprise a storage device interface 331. The storage device interface 331 may be configured to communicate with external storage devices.

Figure 4:
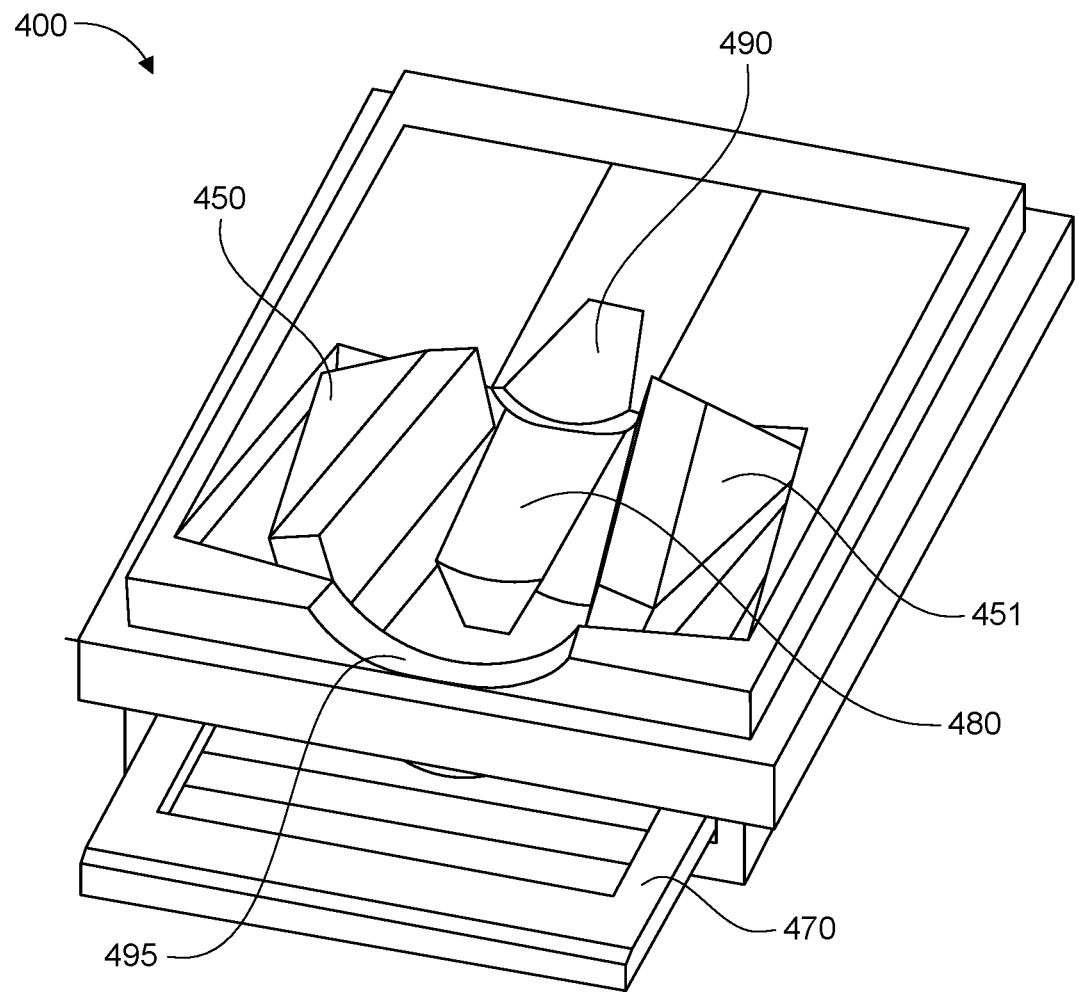
FIG. 4 illustrates a portion of an example adjustable fingerprint capturing device as per an aspect of an embodiment.

FIG. 4 illustrates a portion of an example adjustable fingerprint capturing device 400 as per an aspect of an embodiment. The adjustable fingerprint capturing device 400 may comprise a plurality of moveable finger stabilizers (e.g. 450 and 451), and a stabilizer actuator 470. The adjustable fingerprint capturing device 400 may comprise at least one finger guide (e.g. 490 and 495). The at least one finger guide (e.g. 490 and 495) may comprise at least one concaved surface configured to at least partially conform to the shape of a finger of a subject. The adjustable fingerprint capturing device 400 may comprise at least one moveable finger support plate 480.

Figure 5:
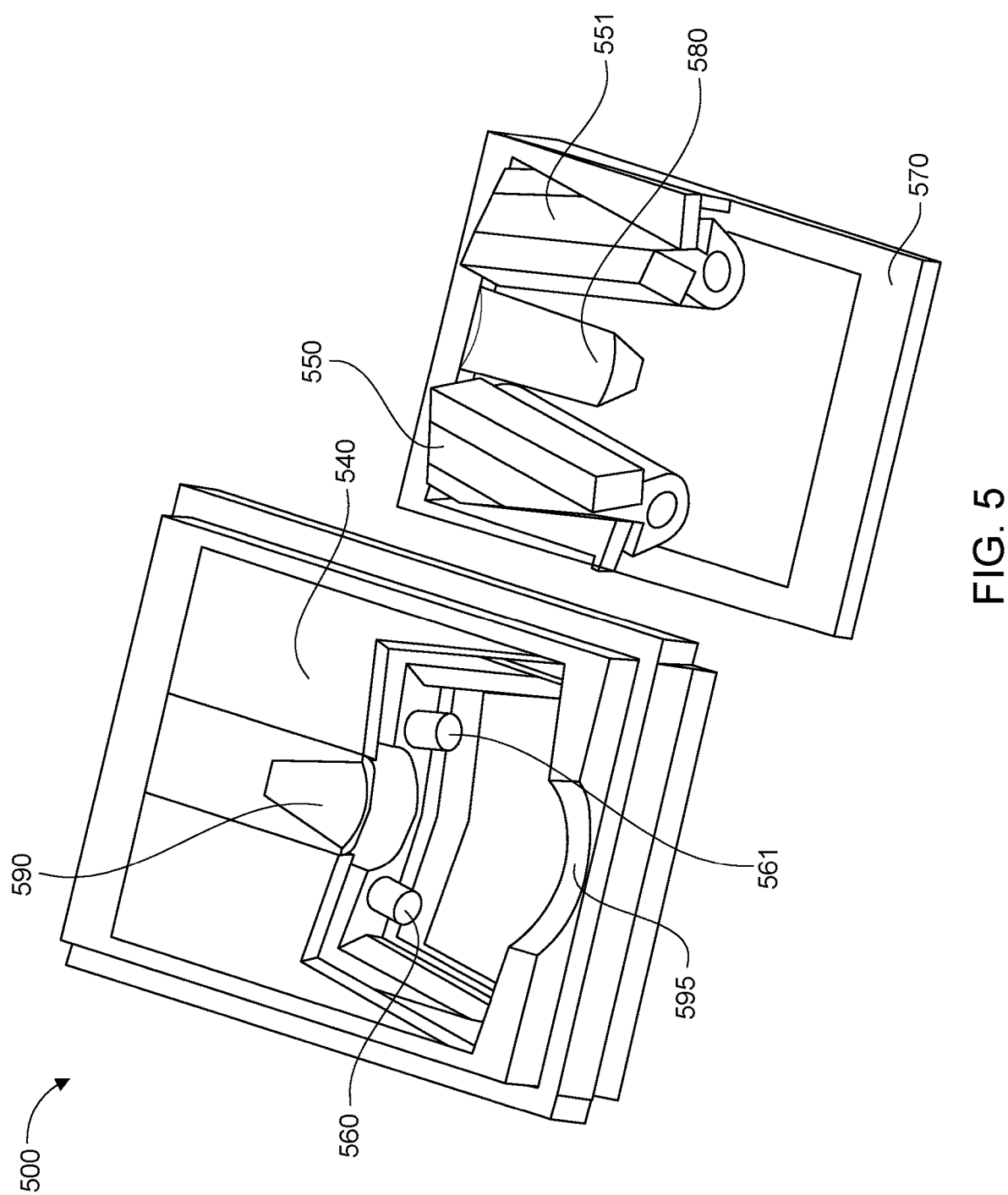
FIG. 5 illustrates a portion of an example adjustable fingerprint capturing device as per an aspect of an embodiment.

FIG. 5 illustrates a portion of an example adjustable fingerprint capturing device 500 as per an aspect of an embodiment. The adjustable fingerprint capturing device 500 may comprise a plurality of moveable finger stabilizers (e.g. 550 and 551), and a stabilizer actuator 570. The adjustable fingerprint capturing device 500 may comprise at least one finger guide (e.g. 590 and 595). The at least one finger guide (e.g. 590 and 595) may comprise at least one concaved surface configured to at least partially conform to the shape of a finger of a subject. Each of at least two of the plurality of moveable finger stabilizers (e.g. 550 and 551) may be configured to rotate around an axis (e.g. 560 and 561). The adjustable fingerprint capturing device 500 may comprise at least one moveable finger support plate (e.g. 580). The at least one moveable finger support plate (e.g. 580) may be configured to move relative to at least a portion of a housing 540. This example illustrates movable finger support plate 580 and moveable finger stabilizers (550 and 551) in a position configured to receive a finger of a subject.

Figure 6:
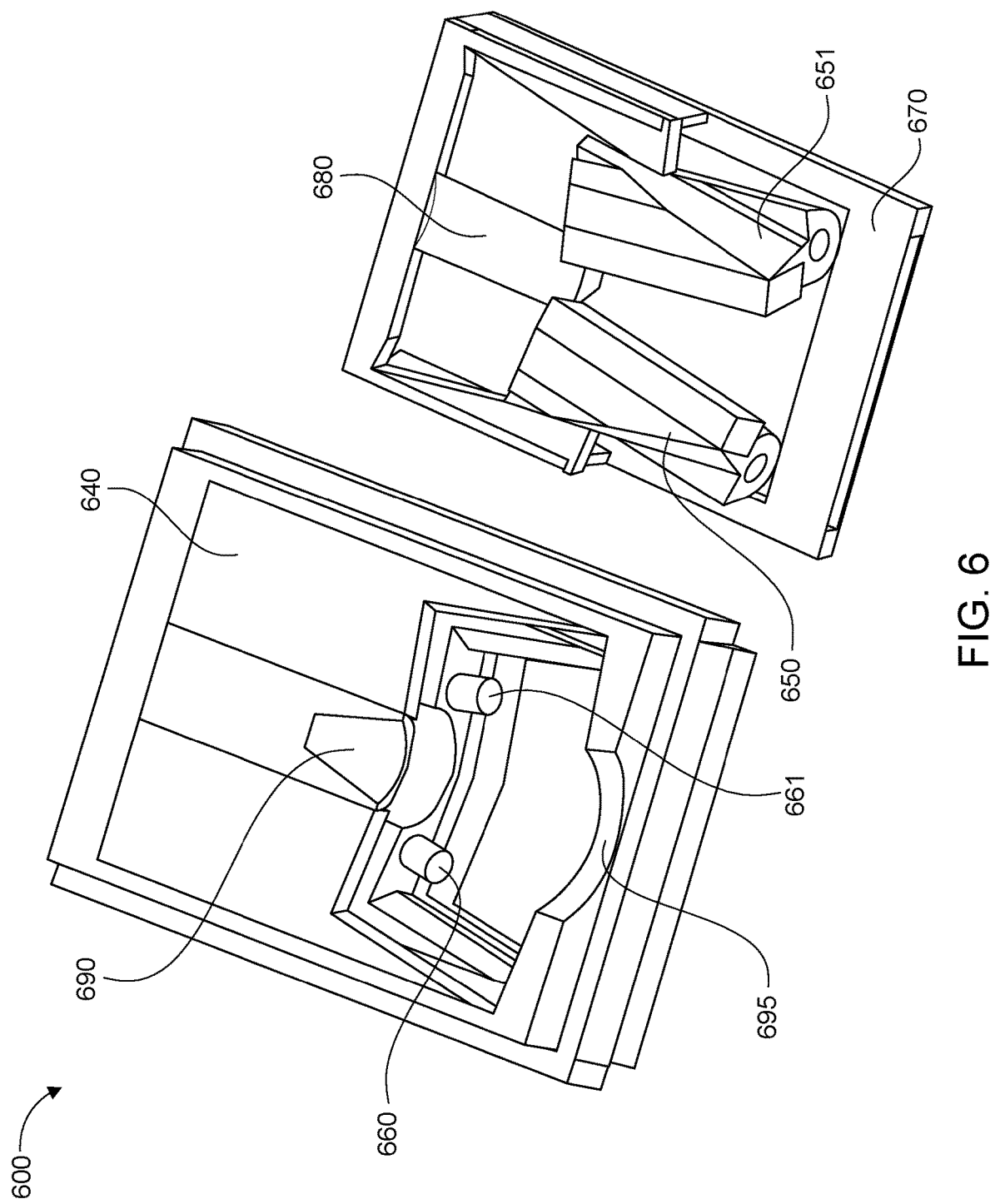
FIG. 6 illustrates a portion of an example adjustable fingerprint capturing device as per an aspect of an embodiment.

FIG. 6 illustrates a portion of an example adjustable fingerprint capturing device 600 as per an aspect of an embodiment. The adjustable fingerprint capturing device 600 may comprise a plurality of moveable finger stabilizers (e.g. 650 and 651), and a stabilizer actuator 670. The adjustable fingerprint capturing device 600 may comprise at least one finger guide (e.g. 690 and 695). The at least one finger guide (e.g. 690 and 695) may comprise at least one concaved surface configured to at least partially conform to the shape of a finger of a subject. Each of at least two of the plurality of moveable finger stabilizers (e.g. 650 and 651) may be configured to rotate around an axis (e.g. 660 and 661). The adjustable fingerprint capturing device 600 may comprise at least one moveable finger support plate (e.g. 680). The at least one moveable finger support plate (e.g. 680) may be configured to move relative to at least a portion of a housing 640. This example illustrates a stabilizer actuator 670 connected to movable finger support plate 680. When inserted into at least a portion of a housing 640, the movable finger support plate 680 may be configured to move out of view of an imaging device disposed under the at least a portion of a housing 640 when the stabilizer actuator 670 is activated. The stabilizer actuator 670 may be activated when pushed into the at least a portion of a housing 640. This example illustrates moveable finger stabilizers (650 and 651) in a position configured to apply pressure to a finger of a subject. The stabilizer actuator 670 may be configured to cause moveable finger stabilizers (650 and 651) to move into the position shown from the position of moveable finger stabilizers (550 and 551) shown in FIG. 5.

According to some of the various embodiments, an adjustable fingerprint capturing device may comprise at least one light source. The at least one light source may be disposed to a housing. The at least one light source may be configured for structured light illumination. The at least one light source may comprise a LED. The at least one light source may comprise at least one LED array. At least one of the at least one light source may be configured to emit at least one light pulse. The adjustable fingerprint capturing device may be configured to capture a plurality of images. At least some of the plurality of images may be captured immediately following each of at least one light pulse from the at least one of the at least one light source. At least some of the plurality of images may be captured immediately following each of at least one light pulse from each of a plurality of light sources. A diffuser may be employed to diffuse light from at least one of the at least one light source. A polarizer may be employed to polarize light from at least one of the at least one light source. The polarizer may be configured to polarize light in the same direction as a polarizer configured to receive reflected light directed towards a lens of at least one imaging device. At least one of the at least one light source may be configured to emit red light, near infrared light, infrared light, combinations thereof, and/or the like. The adjustable fingerprint capturing device may comprise a detector. The detector may be configured to measure the red light, near infrared light, infrared light, combinations thereof, and/or the like. The adjustable fingerprint capturing device may be configured to measure oxygen saturation, deoxygenated hemoglobin, oxygenated hemoglobin, combinations thereof, and/or the like.

According to some of the various embodiments, an adjustable fingerprint capturing device may comprise at least one power source. The at least one power source may comprise a battery, a biofuel cell, a solar panel, combinations thereof, and/or the like. The adjustable fingerprint capturing device may comprise a charging receiver. The charging receiver may be configured to receive power and transfer at least part of the power to at least one power source. The charging receiver may be configured to receive power through employment of a wired connection. The charging receiver may be configured to receive power wirelessly. The charging receiver may comprise at least one induction coil.

According to some of the various embodiments, an adjustable fingerprint capturing device may comprise at least one transceiver. The at least one transceiver may be configured to communicate with a controller, at least one imaging device, at least one computing device, at least one remote device, combinations thereof, and/or the like. The at least one transceiver may be configured to communicate through employment of a Bluetooth connection, Wi-Fi network, a cellular network, combinations thereof, and/or the like. The adjustable fingerprint capturing device may comprise at least one modem. The at least one modem may be configured to communicate with a controller, at least one imaging device, at least one computing device, at least one remote device, combinations thereof, and/or the like. The at least one modem may be configured to communicate through employment of an Ethernet connection, a serial connection (for example USB, Thunderbolt, SATA, SCSI), combinations thereof, and/or the like. The adjustable fingerprint capturing device may comprise at least one audio and/or video interface. The at least one audio and/or video interface may comprise an HDMI interface, a DisplayPort interface, a DVI interface, combinations thereof, and/or the like.

According to some of the various embodiments, an adjustable fingerprint capturing device may comprise at least one filter. At least one of the at least one filter may be disposed to at least one imaging device. At least one of the at least one filter may be disposed to at least one light source. The adjustable fingerprint capturing device may comprise at least one polarizer. The at least one polarizer may be employed to polarize reflected light prior to being received in a lens of at least one of the at least one imaging device. At least one of the at least one polarizer may be disposed to at least one of the at least one imaging device. At least one of the at least one polarizer may be disposed to at least one of at least one light source. The at least one polarizer disposed to the at least one imaging device may be parallel to the at least one polarizer disposed to the at least one light source. The at least one polarizer disposed to the at least one imaging device may be configured to polarize reflected light parallel to polarized light emitted from the at least one light source.

Figure 7:
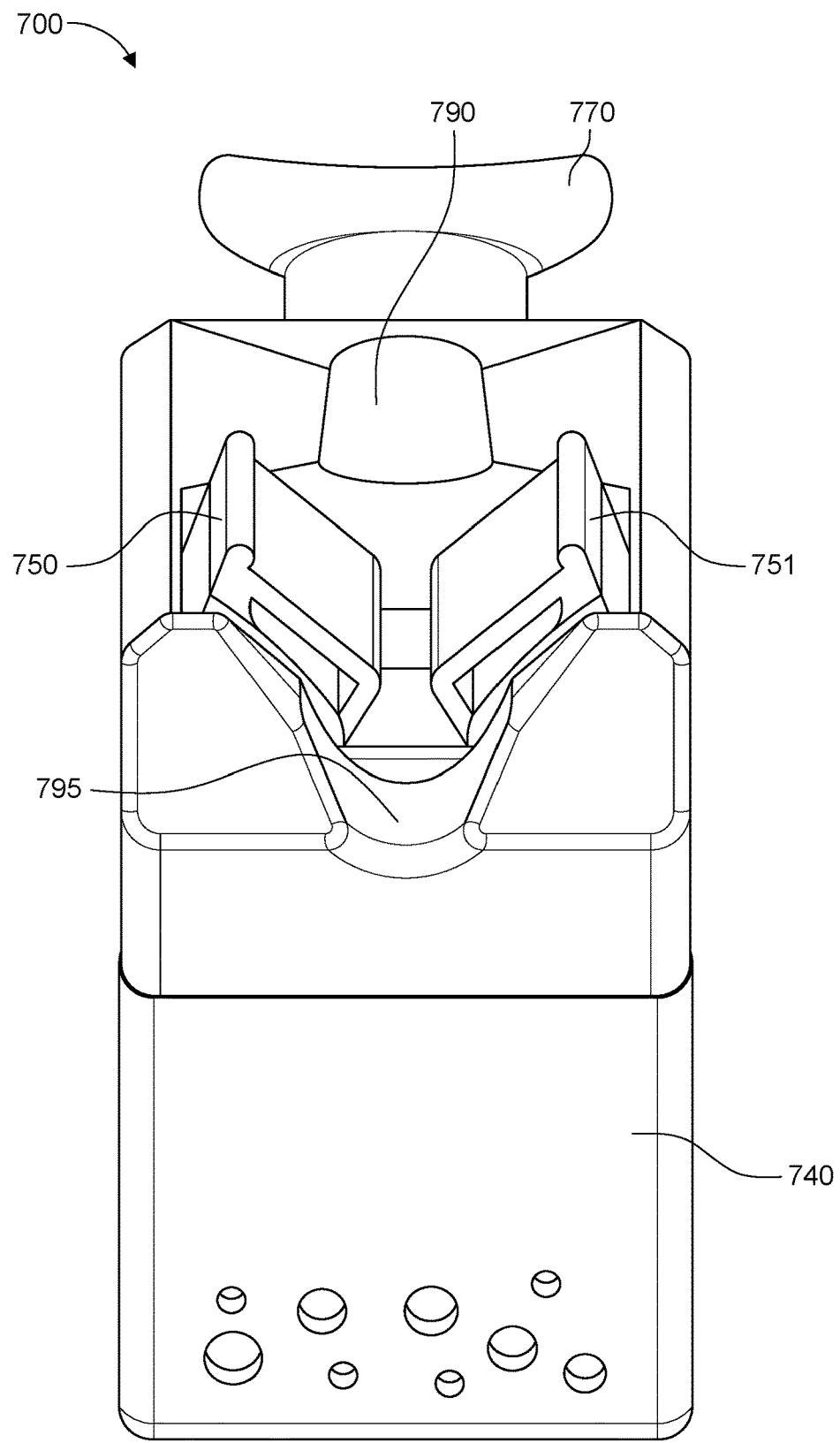
FIG. 7 illustrates an example adjustable fingerprint capturing device as per an aspect of an embodiment.

FIG. 7 illustrates an example adjustable fingerprint capturing device 700 as per an aspect of an embodiment. The adjustable fingerprint capturing device 700 may comprise a housing 740, a plurality of moveable finger stabilizers (e.g. 750 and 751), and a stabilizer actuator 740. The adjustable fingerprint capturing device 700 may comprise at least one finger guide (e.g. 790 and 795). The at least one finger guide (e.g. 790 and 795) may comprise at least one concaved surface configured to at least partially conform to the shape of a finger of a subject. This example illustrates moveable finger stabilizers (750 and 751) in a position configured to receive a finger of a subject.

Figure 8:
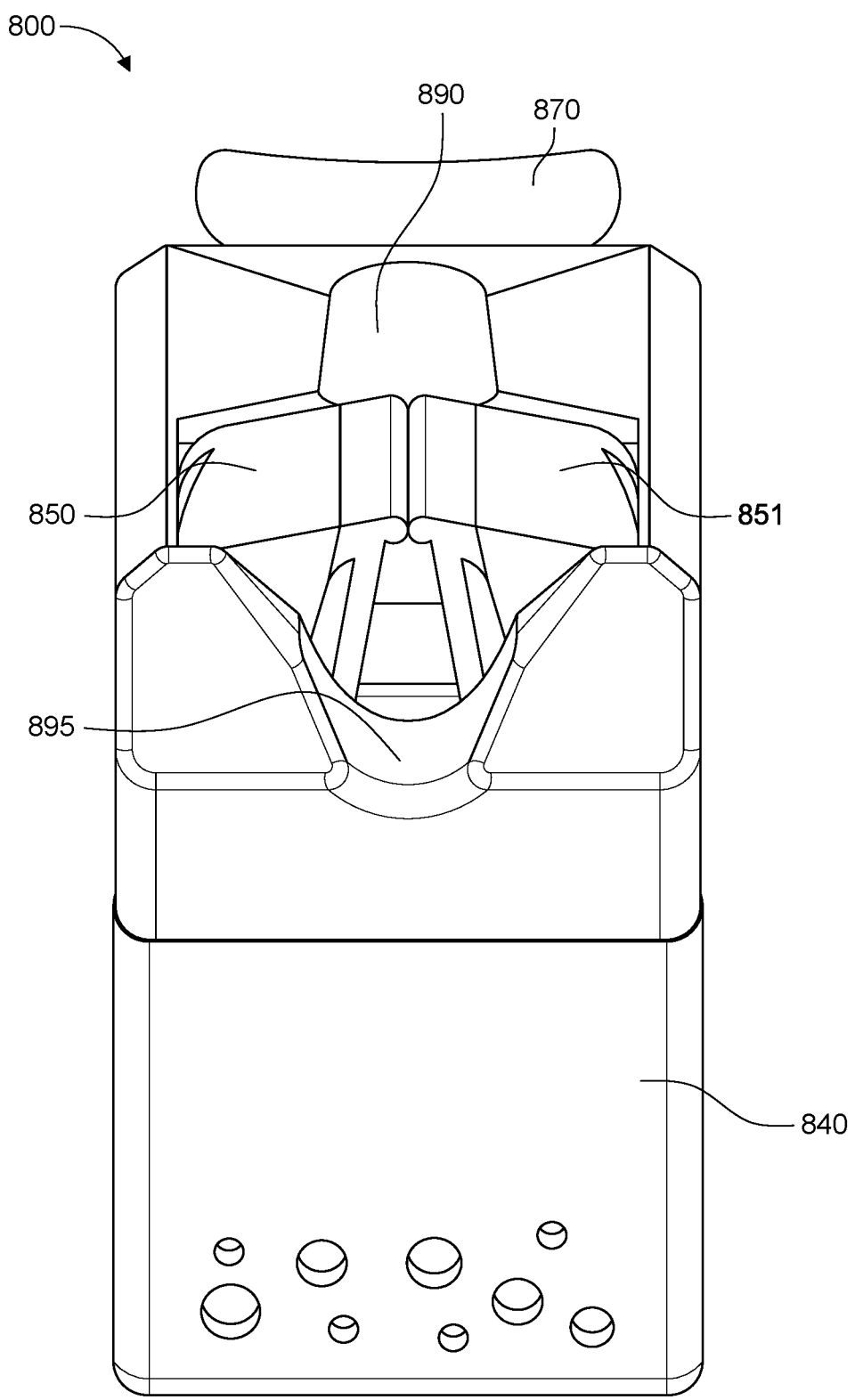
FIG. 8 illustrates an example adjustable fingerprint capturing device as per an aspect of an embodiment.

FIG. 8 illustrates an example adjustable fingerprint capturing device 800 as per an aspect of an embodiment. The adjustable fingerprint capturing device 800 may comprise a housing 840, a plurality of moveable finger stabilizers (e.g. 850 and 851), and a stabilizer actuator 870. The adjustable fingerprint capturing device 800 may comprise at least one finger guide (e.g. 890 and 895). The at least one finger guide (e.g. 890 and 895) may comprise at least one concaved surface configured to at least partially conform to the shape of a finger of a subject. Each of at least two of the plurality of moveable finger stabilizers (e.g. 850 and 851) may be configured to rotate around an axis (not shown). This example illustrates a stabilizer actuator 870 in an activated position. The stabilizer actuator 870 may be activated when pushed into housing 840. This example illustrates moveable finger stabilizers (850 and 851) in a position configured to apply pressure to a finger of a subject. The stabilizer actuator 870 may be configured to cause moveable finger stabilizers (850 and 851) to move into the position shown from the position of moveable finger stabilizers (750 and 751) shown in FIG. 7.

Figure 9:
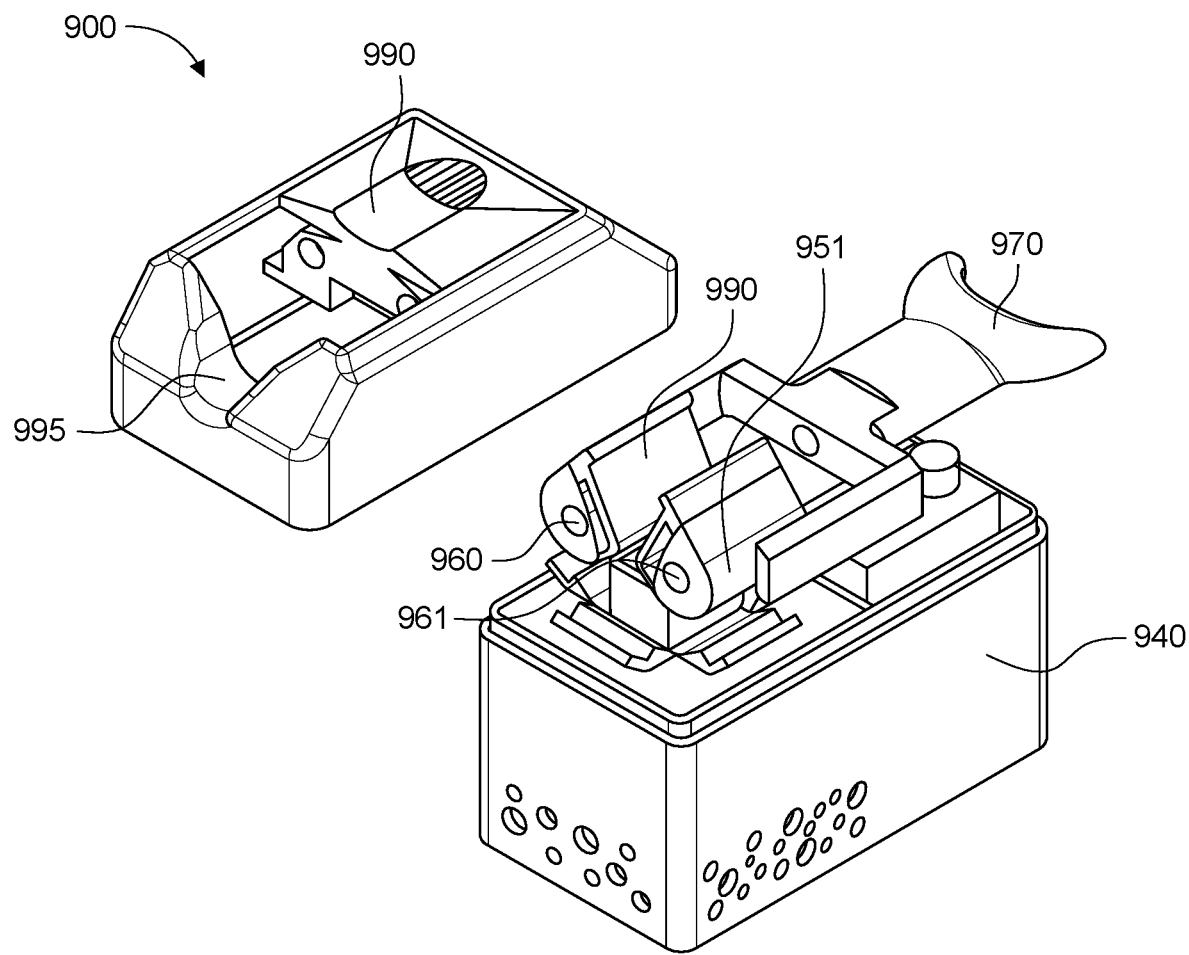
FIG. 9 illustrates an example adjustable fingerprint capturing device as per an aspect of an embodiment.

FIG. 9 illustrates an example adjustable fingerprint capturing device 900 as per an aspect of an embodiment. The adjustable fingerprint capturing device 900 may comprise a housing 940, a plurality of moveable finger stabilizers (e.g. 950 and 951), and a stabilizer actuator 970. The adjustable fingerprint capturing device 900 may comprise at least one finger guide (e.g. 990 and 995). The at least one finger guide (e.g. 990 and 995) may comprise at least one concaved surface configured to at least partially conform to the shape of a finger of a subject. Each of at least two of the plurality of moveable finger stabilizers (e.g. 950 and 951) may be configured to rotate around an axis (e.g. 960 and 961). This example illustrates moveable finger stabilizers (950 and 951) in a position configured to receive a finger of a subject.

Figure 10:
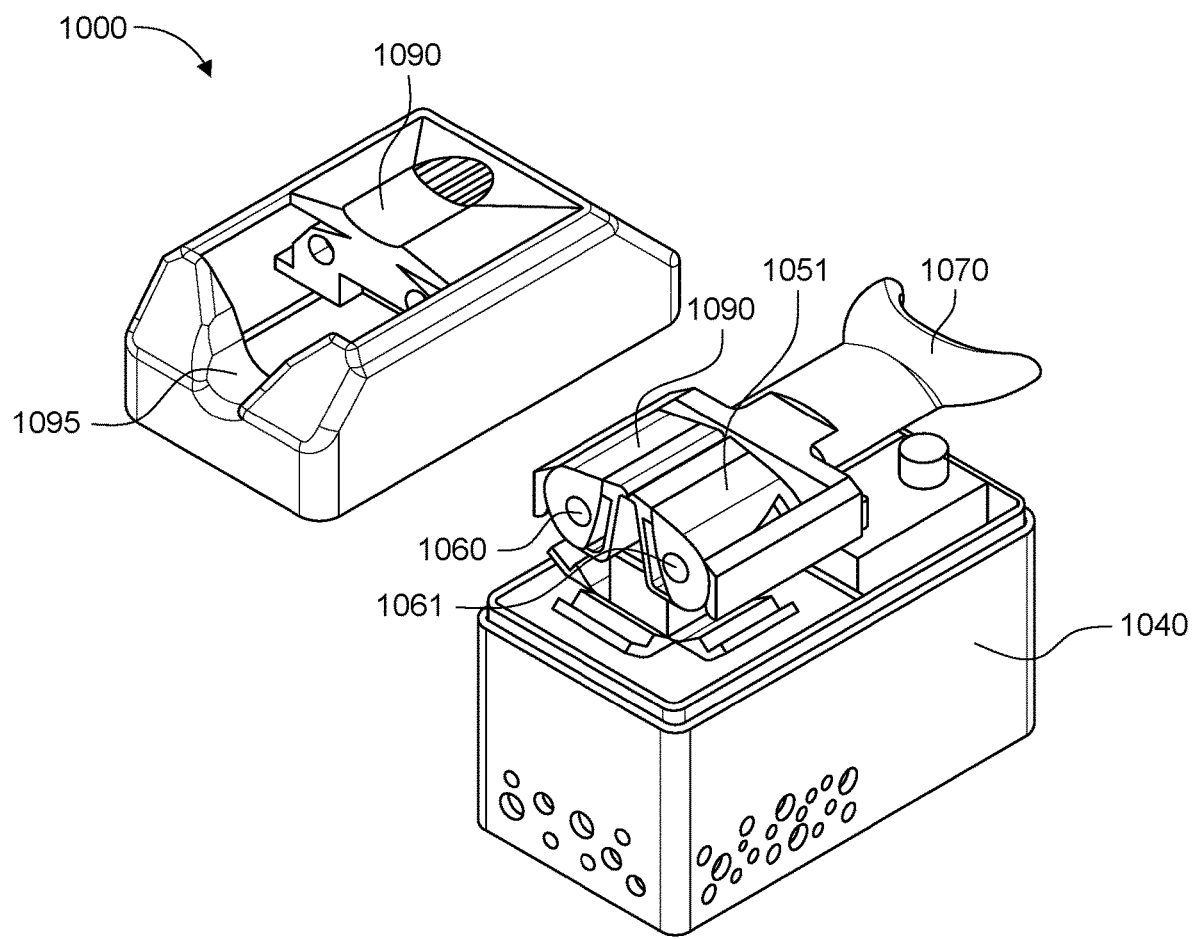
FIG. 10 illustrates an example adjustable fingerprint capturing device as per an aspect of an embodiment.

FIG. 10 illustrates an example adjustable fingerprint capturing device 1000 as per an aspect of an embodiment. The adjustable fingerprint capturing device 1000 may comprise a housing 1040, a plurality of moveable finger stabilizers (e.g. 1050 and 1051), and a stabilizer actuator 1070. The adjustable fingerprint capturing device 1000 may comprise at least one finger guide (e.g.1090 and 1095). The at least one finger guide (e.g. 1090 and 1095) may comprise at least one concaved surface configured to at least partially conform to the shape of a finger of a subject. Each of at least two of the plurality of moveable finger stabilizers (e.g. 1050 and 1051) may be configured to rotate around an axis (e.g. 1060 and 1061). This example illustrates a stabilizer actuator 1070 in an activated position. The stabilizer actuator 1070 may be activated when pushed into housing 1040. This example illustrates moveable finger stabilizers (1050 and 1051) in a position configured to apply pressure to a finger of a subject. The stabilizer actuator 1070 may be configured to cause moveable finger stabilizers (1050 and 1051) to move into the position shown from the position of moveable finger stabilizers (950 and 951) shown in FIG. 9.

According to some of the various embodiments, a method of capturing at least one image of a finger of a subject may comprise placing the finger of the subject in between at least two of a plurality of moveable finger stabilizers. The plurality of moveable finger stabilizers may be configured to move about a portion of a housing disposed to the plurality of moveable finger stabilizers. The plurality of moveable finger stabilizers may be configured to apply pressure to the finger of the subject. The method may comprise activating a stabilizer actuator. The stabilizer actuator may be connected to the housing and the plurality of moveable finger stabilizers. The stabilizer activator may be configured to cause the plurality of moveable finger stabilizers to move. The stabilizer activator may be configured to cause the plurality of moveable finger stabilizers to move towards the finger of the subject. The stabilizer activator may be configured to cause the plurality of moveable finger stabilizers to move away from the finger of the subject. The stabilizer actuator may be connected to at least one moveable finger support plate. The stabilizer actuator may be configured to cause the at least one moveable finger support plate to move. The method may comprise activating an image actuator configured to communicate a capture signal to at least one imaging device. The capture signal may be communicated through employment of a wireless and/or wired connection. The method may comprise capturing at least one fingerprint of the subject through employment of the at least one imaging device.

According to some of the various embodiments, a method of capturing at least one image of a finger of a subject may comprise converting at least one fingerprint into at least one fingerprint feature map. The method may comprise creating a biometric indexed health record comprising data related to at least one medical treatment administered to the subject. The method may comprise storing data associated with at least one of the at least one fingerprint. The data may be accessible to the biometric indexed health record. The data may be accessible to a health record.

Figure 11:
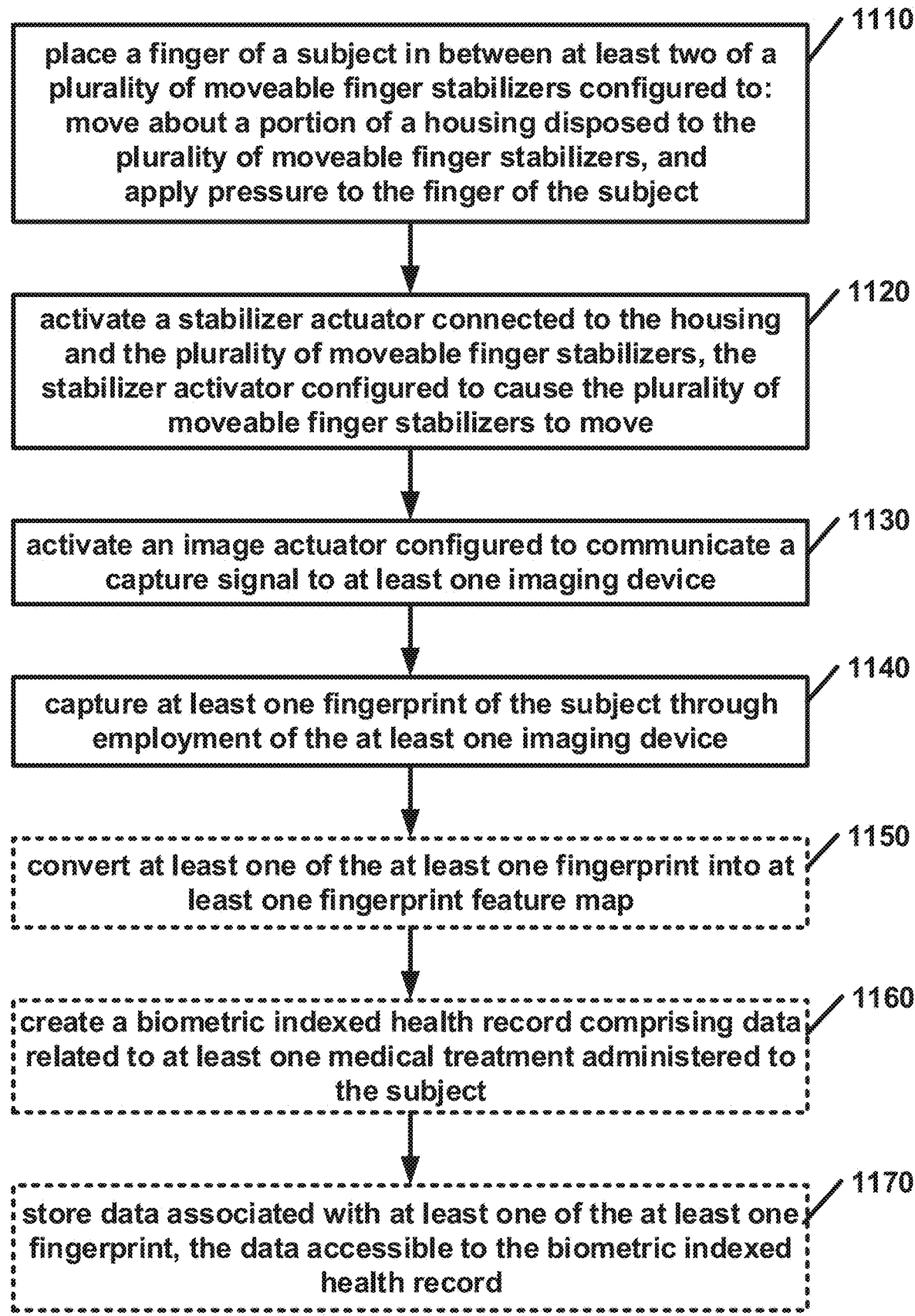
FIG. 11 is an example flow diagram of capturing at least one fingerprint according to various aspects of various embodiments.

FIG. 11 is an example flow diagram of capturing at least one fingerprint according to various aspects of various embodiments. A finger of a subject may be placed in between at least two of a plurality of moveable finger stabilizers at 1110. The at least two of a plurality of moveable finger stabilizers may be configured to move about a portion of a housing disposed to the plurality of moveable finger stabilizers. The at least two of a plurality of moveable finger stabilizers may be configured to apply pressure to the finger of the subject. A stabilizer actuator connected to the housing and the plurality of moveable finger stabilizers may be activated at 1120. The stabilizer activator may be configured to cause the plurality of moveable finger stabilizers to move. An image actuator configured to communicate a capture signal to at least one imaging device may be activated at 1130. At least one fingerprint of the subject may be captured through employment of the at least one imaging device at 1140. At least one of the at least one fingerprint may be converted into at least one fingerprint feature map at 1150. A biometric indexed health record comprising data related to at least one medical treatment administered to the subject may be created at 1160. Data associated with at least one of the at least one fingerprint may be stored at 1170. The data may be accessible to the biometric indexed health record.

Figure 12:
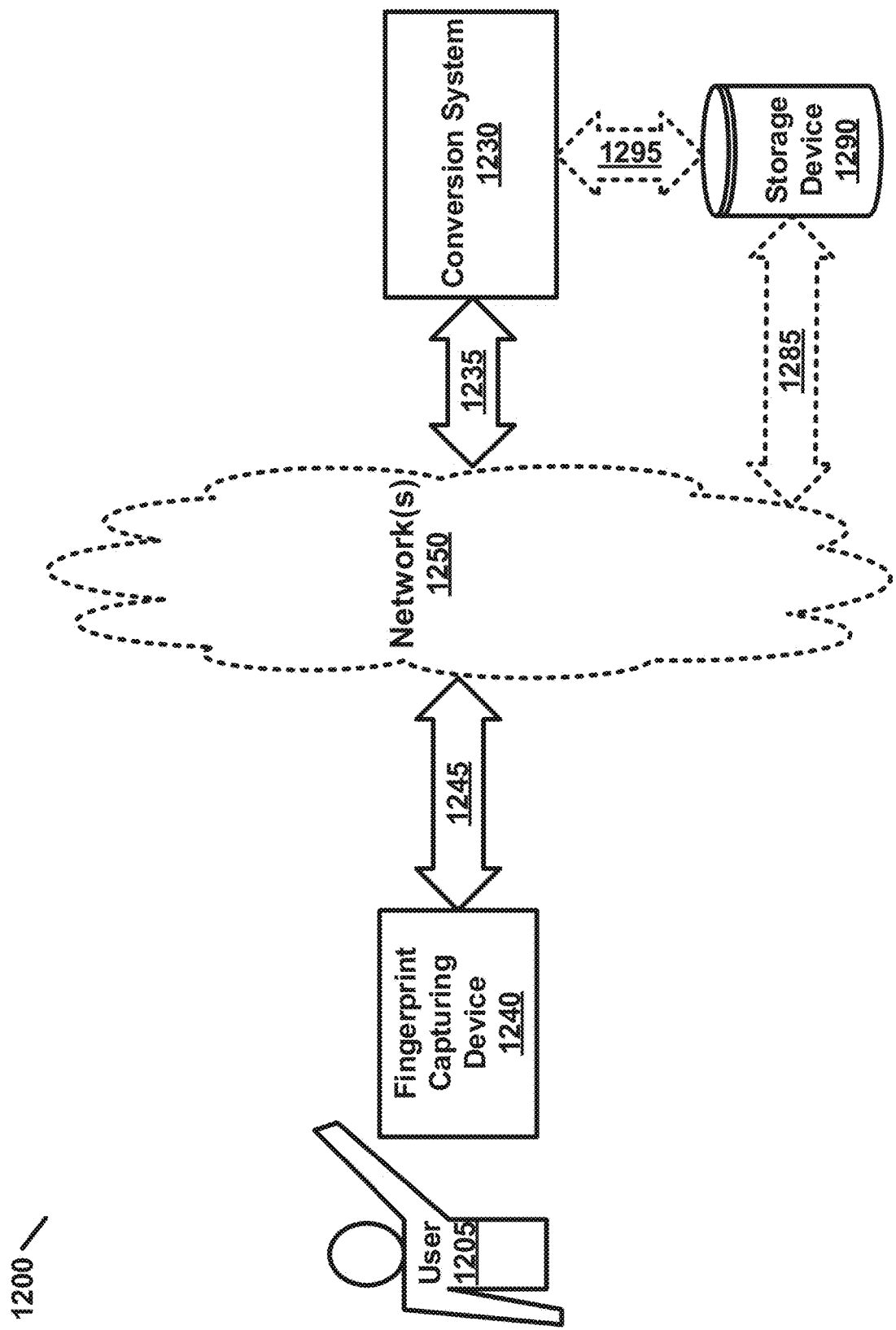
FIG. 12 is an example block diagram showing a fingerprint capturing device system according to various aspects of various embodiments.

FIG. 12 is an example block diagram showing a fingerprint capturing device system 1200 according to various aspects of various embodiments. The fingerprint capturing device system 1200 may comprise a fingerprint capturing device 1240 and a conversion system 1230. The fingerprint capturing device 1240 may be configured for operation by user 1205. The conversion system 1230 may be configured to convert at least one fingerprint into at least one fingerprint feature map. The fingerprint capturing device 1240 may be configured to communicate with the conversion system 1230. At least one network (e.g. 1250) may be employed for communication between the fingerprint capturing device 1240 and the conversion system 1230. Network connection 1245 may be employed for communication between the fingerprint capturing device 1240 and one of the at least one network (e.g. 1250). Network connection 1235 may be employed for communication between the conversion system 1230 and one of the at least one network (e.g. 1250). The network connection 1245 and the network connection 1235 may be the same. For example, fingerprint capturing device 1240 may be configured to communicate directly with the conversion system 1230. The fingerprint capturing device system 1200 may comprise a storage device 1290. The conversion system 1230 may be configured to communicate with the storage device 1290 through employment of connection 1295. The fingerprint capturing device 1240 may be configured to communicate with the storage device 1290 through employment of network connection 1285. The network connection 1245 and the network connection 1285 may be the same. For example, fingerprint capturing device 1240 may be configured to communicate directly with the storage device 1290.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In this specification, "a" and "an" and similar phrases are to be interpreted as "at least one" and "one or more." References to "a", "an", and "one" are not to be interpreted as "only one". References to "an" embodiment in this disclosure are not necessarily to the same embodiment.

Some of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e. hardware with a biological element) or a combination thereof, all of which are behaviorally equivalent. For example, modules may be implemented using computer hardware in combination with software routine(s) written in a computer language (Java, HTML, XML, PHP, Python, ActionScript, JavaScript, Ruby, Prolog, SQL, VBScript, Visual Basic, Perl, C, C++, Objective-C or the like). Additionally, it may be possible to implement modules using physical hardware that incorporates discrete or programmable analog, digital and/or quantum hardware.

Examples of programmable hardware include: computers, microcontrollers, microprocessors, application-specific integrated circuits (ASICs), field programmable gate arrays (FPGAs), and complex programmable logic devices (CPLDs). Computers, microcontrollers and microprocessors may be programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies may be used in combination to achieve the result of a functional module.

Some embodiments may employ processing hardware. Processing hardware may include one or more processors, computer equipment, embedded system, machines and/or the like. The processing hardware may be configured to execute instructions. The instructions may be stored on a machine-readable medium. According to some embodiments, the machine-readable medium (e.g. automated data medium) may be a medium configured to store data in a machine-readable format that may be accessed by an automated sensing device. Examples of machine-readable media include: magnetic disks, cards, tapes, and drums, flash memory, memory cards, electrically erasable programmable read-only memory (EEPROM), solid state drives, optical disks, barcodes, magnetic ink characters, and/or the like.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112. Claims that do not expressly include the phrase "means for" or "step for" are not to be interpreted under 35 U.S.C. 112.

What is claimed is:

1. An adjustable fingerprint capturing device configured to stabilize a finger of a subject, the adjustable fingerprint capturing device comprising:
   at least one imaging device configured to capture at least one image of the finger of the subject;
   an image actuator;
   a controller configured to activate the at least one imaging device based on input from the image actuator;
   a housing disposed to the at least one imaging device, the image actuator, and the controller;
   a plurality of moveable finger stabilizers, configured to:
      move about a portion of the housing; and
      apply pressure to the finger of the subject; and
   a stabilizer actuator:
      connected to the housing and the plurality of moveable finger stabilizers;
      configured to cause the plurality of moveable finger stabilizers to move;
      wherein the stabilizer actuator comprises at least one of the following: a lever;
      a pin; a gear; an electromechanical device; and a trigger; and
      wherein at least one of the lever and the pin is configured to cause the plurality of moveable finger stabilizers to move towards the finger of the subject upon receiving pressure on at least one of the lever and the pin from an operator of the adjustable fingerprint capturing device.

2. The adjustable fingerprint capturing device according to claim 1, wherein at least one of the at least one imaging device comprises at least one of:
   a camera, an ultrasound device, and at least one liquid lens.

3. The adjustable fingerprint capturing device according to claim 1, wherein the housing comprises at least one finger guide comprising at least one concaved surface configured to at least partially conform to the shape of the finger of the subject.

4. The adjustable fingerprint capturing device according to claim 1, wherein the finger stabilizer is configured to position the finger of the subject in a location suitable for a successful fingerprint capture through employment of at least one of the at least one imaging device.

5. The adjustable fingerprint capturing device according to claim 1, wherein at least two of the plurality of moveable finger stabilizers are configured to move along a portion of the housing.

6. The adjustable fingerprint capturing device according to claim 1, wherein at least two of the plurality of moveable finger stabilizers are configured to apply pressure to the sides of the finger of the subject.

7. The adjustable fingerprint capturing device according to claim 1, wherein the stabilizer actuator is configured to cause activation of the image actuator.

8. The adjustable fingerprint capturing device according to claim 1, wherein the subject comprises one of:
   a. an infant; and
   b. a toddler.

9. An adjustable fingerprint capturing device configured to stabilize a finger of a subject, the adjustable fingerprint capturing device comprising:
   at least one imaging device configured to capture at least one image of the finger of the subject;
   an image actuator;
   a controller configured to activate the at least one imaging device based on input from the image actuator;
   a housing disposed to the at least one imaging device, the image actuator, and the controller;
   a plurality of moveable finger stabilizers, configured to:
      move about a portion of the housing; and
      apply pressure to the finger of the subject; and
   a stabilizer actuator:
      connected to the housing and the plurality of moveable finger stabilizers;

configured to cause the plurality of moveable finger stabilizers to move;
wherein the stabilizer actuator comprises at least one of the following: a lever; a pin; a gear; an electromechanical device; and a trigger; and
wherein at least one of the lever and the pin is configured to cause the plurality of moveable finger stabilizers to move away from the finger of the subject upon a reduction of pressure on at least one of the lever and the pin from an operator of the adjustable fingerprint capturing device.

10. The adjustable fingerprint capturing device according to claim 1, further comprising at least one moveable finger support plate configured to support at least a portion of the palmar surface of the fingertip of the finger of the subject.

11. The adjustable fingerprint capturing device according to claim 10, wherein the stabilizer actuator is further configured to cause the at least one moveable support plate to move.

12. The adjustable fingerprint capturing device according to claim 1, further comprising at least one fixed finger stabilizer configured to apply pressure to the tip of the finger of the subject.

13. The adjustable fingerprint capturing device according to claim 1, further comprising at least one light source disposed to the housing.

14. A method of capturing at least one image of a finger of a subject, the method comprising:
a. placing the finger of the subject in between at least two of a plurality of moveable finger stabilizers configured to:
  i. move about a portion of a housing disposed to the plurality of moveable finger stabilizers;
  ii. apply pressure to the finger of the subject; and
  iii. rotate around an axis connected to the housing;
b. activating a stabilizer actuator connected to the housing and the plurality of moveable finger stabilizers, the stabilizer activator configured to cause the plurality of moveable finger stabilizers to move, wherein the stabilizer actuator comprises at least one of the following: a lever; a pin; a gear; an electromechanical device; and a trigger, wherein at least one of the lever and the pin is configured to cause the plurality of moveable finger stabilizers to move towards the finger of the subject upon receiving pressure on at least one of the lever and the pin from an operator of the adjustable fingerprint capturing device;
c. activating an image actuator configured to communicate a capture signal to at least one imaging device; and
d. capturing at least one fingerprint of the subject through employment of the at least one imaging device.

15. The method according to claim 14, wherein the stabilizer actuator is further connected to at least one moveable finger support plate, and the stabilizer actuator is further configured to cause the at least one moveable finger support plate to move.

16. The method according to claim 14, further comprising converting at least one of the at least one fingerprint into at least one fingerprint feature map.

17. The method according to claim 14, further comprising:
a. creating a biometric indexed health record comprising data related to at least one medical treatment administered to the subject; and
b. storing data associated with at least one of the at least one fingerprint, the data accessible to the biometric indexed health record.

18. The method according to claim 14, further comprising storing data associated with at least one of the at least one fingerprint, the data accessible to a biometric indexed health record.

19. The method according to claim 14, further comprising storing data associated with at least one of the at least one fingerprint, the data accessible to a health record.

20. A method of capturing at least one image of a finger of a subject, the method comprising:
a. placing the finger of the subject in between at least two of a plurality of moveable finger stabilizers configured to:
  i. move about a portion of a housing disposed to the plurality of moveable finger stabilizers;
  ii. apply pressure to the finger of the subject; and
  iii. rotate around an axis connected to the housing;
b. activating a stabilizer actuator connected to the housing and the plurality of moveable finger stabilizers, the stabilizer activator configured to cause the plurality of moveable finger stabilizers to move, wherein the stabilizer actuator comprises at least one of the following: a lever; a pin; a gear; an electromechanical device; and a trigger, wherein at least one of the lever and the pin is configured to cause the plurality of moveable finger stabilizers to move away from the finger of the subject upon a reduction of pressure on at least one of the lever and the pin from an operator of the adjustable fingerprint capturing device;
c. activating an image actuator configured to communicate a capture signal to at least one imaging device; and
d. capturing at least one fingerprint of the subject through employment of the at least one imaging device.

21. The adjustable fingerprint capturing device according to claim 1, wherein each of at least two of the plurality of moveable finger stabilizers are configured to rotate around an axis connected to the housing.

* * * * *